United States Patent [19]

Hassinger

[11] Patent Number: Plant 6,655

[45] Date of Patent: Mar. 7, 1989

[54] YELLOW LEAF FORSYTHIA 'CLEMS'

[76] Inventor: Clarence Hassinger, Road #1, Mercer, Pa. 16137

[21] Appl. No.: 90,897

[22] Filed: Aug. 31, 1987

[51] Int. Cl.[4] ..... A01H 5/00

[52] U.S. Cl. ..... Plt./54

[58] Field of Search ..... Plt./54

[56] References Cited

PUBLICATIONS

Bailey, L. H. (1935) The Standard Cyclopedia of Horticulture (vol. 2), "Forsythia", The MacMillan Co., N.Y., pp. 1268 and 1269 being cited.

Exotica 3, Alfred Graf, Roehrs Company, Rutherford, NJ, Copin, 1963.

*Primary Examiner*—James R. Feyrer

*Attorney, Agent, or Firm*—Larson & Taylor

[57] ABSTRACT

A new and distinct selection of Forsythia which hereinafter shall be referred to as Clems Yellow Leaf Forsythia. Clems Yellow Leaf Forsythia differs from other selections of Forsythia by possessing unique yellow foliage on the new growth up to 18 inches back on the branches, darker green mature foliage from the base up to the final 18 inches of the branches, leaf arrangements of two different types on the same shrub, and yellow blossoms in the spring.

2 Drawing Sheets

DISCOVERY

This invention relates to a new and distinct selection of Forsythia. This selection was discovered by me, Clarence E. Hassinger, at Clems Nursery, Rural Delivery #1, Mercer, Pa., 16137 as a sport growing on the nursery property.

The plant to date is known to exist only within the boundaries of Clems Nursery, Rural Delivery #1, Mercer, Pa. 16137.

The selection has not been offered for sale or described in any publication.

TRADE NAME

The selection will be sold under the trade name Clems Yellow Leaf Forsythia.

REPRODUCTION

This new and distinct selection has been strictly asexually reproduced by cuttings at Clems Nursery. Sexual reproduction, such as seed propagation has not been attempted, since no seed has formed on the plant. Grafting has not been attempted.

The selection has been produced asexually in large amounts and in each case the resulting plants have exhibited the distinguishing characteristics of the parent plant, indicating that the new variety is well established. The selection has been asexually reproduced through three generations.

CHARACTERISTICS

Figure 1:
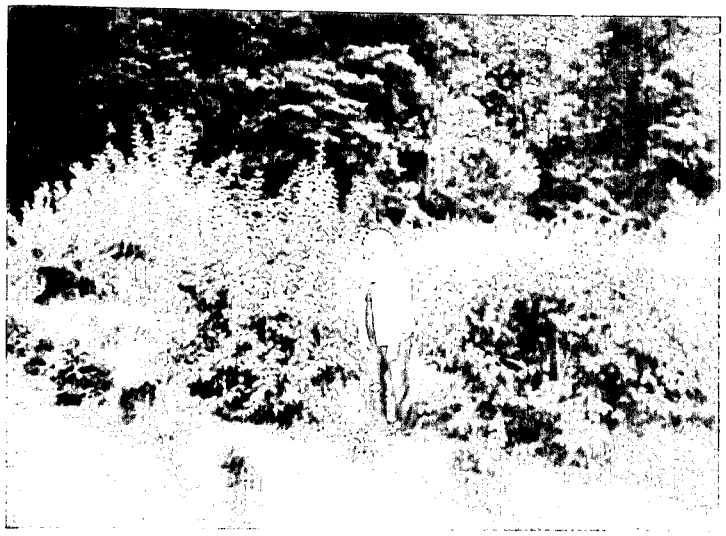
FIG. 1 labeled selection shows the inventors wife with a specimen of Clems Yellow Leaf Forsythia to her right.
Figure 2:
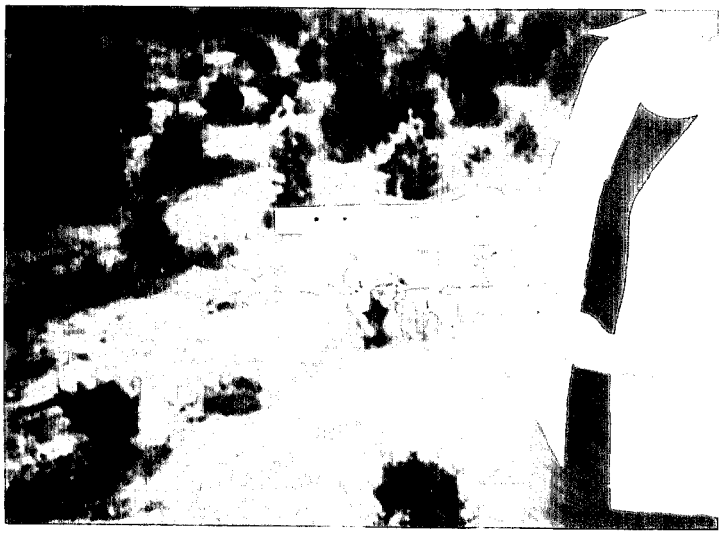
FIG. 2 displays a branch from a Clems Yellow Leaf Forsythia next to a 12 inch ruler.
Figure 3:
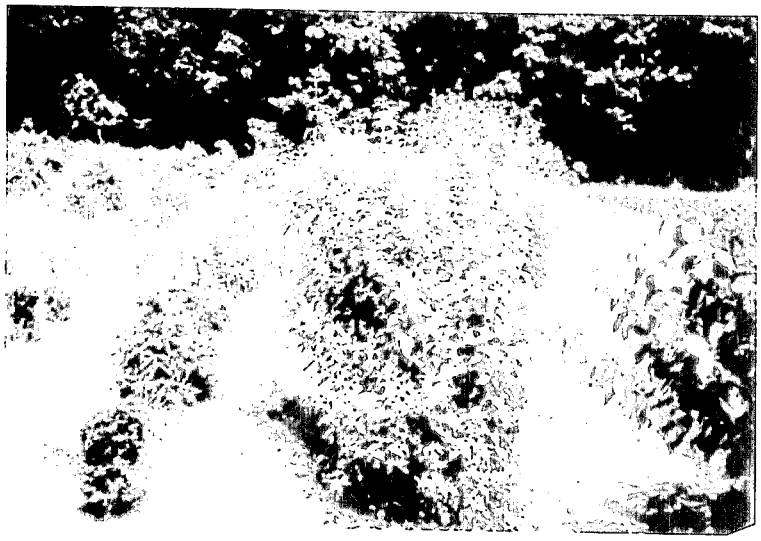
FIG. 3 shows a four year old Clems Yellow Leaf Forsythia which has been asexually reproduced from the parent plant by cuttings.

Clems Yellow Leaf Forsythia differs from other Forsythia as listed below:

1. The new selection has yellow foliage on the new growth 18" back on the branches. The color is #503/2 Barium Yellow 90% mottled with Agathia Green #60 10%.

2. At 18" back on the branches the color gradually darkens until the mature foliage is a Spinach Green #0960.

3. The leaves are of two types on the same shrub. The leaves may be of two types on the same branch. One type is a simple leaf opposite. The other type is a tri-partite leaf opposite.

4. The selection produces yellow blossoms in the spring.

COMPARISON WITH *Forsythia intermedia*

Clem's Yellow Leaf Forsythia blooms at approximately the same time as *intermedia* but drops its blossoms about four days ahead of *intermeida.*

Clem's Yellow Leaf Forsythia is hardy in Zone 5 and the flower buds have successfully withstood temperatures down to −15° F. for a period of three to five days.

The leaves are similar to *intermeida* in size and type. The flowers are in clusters of one to six with four flowers being an average cluster. The clusters are about one inch apart on the branches. Clem's Yellow Leaf Forsythia has been asexually reproduced for four generations and does not appear to be affected by disease or insects. It is a fast-growing plant which reaches a height of seven feet in four years and the plant flowers to the ends of the branches without crowding at the base.

DESCRIPTION

Below is a detailed description of the new selection. All colors used are from the British Horticultural Colour Charts issued by the British Colour Council in collaboration with The Royal Horticultural Society.

It is believed that the species of the plant is *Forsythia intermedia.*

Overall size habit: The mature shrub is approximately 11 feet high and 10 feet wide. The mature plant is vase shaped.

Mature foliage at base or center of shrub:

*Shape.*—Oval-elliptical.
*Tip.*—Pointed.
*Margin.*—Dentate.
*Width.*—4.5 to 5.5 millimeters.
*Length.*—6 to 9 millimeters.
*Arrangement.*—Opposite and simple; and opposite and tri-partite.
*Petiole.*—Slightly arching.
*Color.*—Spinach Green #0960.

New growth foliage from tip to 18 inches back on branch:
*Shape.*—Oval-elliptical.
*Tip.*—Pointed.
*Margin.*—Dentate.
*Width.*—1.5 to 3 millimeters.
*Length.*—1.5 to 8 millimeters.
*Arrangement.*—Tri-partite and opposite.
*Color.*—Mottled 90% Barium Yellow Color #503/2 and 10% Agathia Green #60.

Flower:
*Bloom.*—Early spring.
*Calyx.*—Deeply four lobed and the color is Canary Yellow #2.
*Corolla lobes.*—Deeply four lobed, the lobes are veined on the interior surface, are ¾″ long from the point they divide from the campanulate tube and are 7/16″ wide at their widest point. The color of the corolla lobes is Canary Yellow #2 and the lobes are longer than the campanulate tube.
*Color.*—Canary yellow #2.
*Spacing.*—½ to 1 inch opposite.

*Speed.*—None apparent.
*Stamen.*—Two stamen are attached to the base of the corolla. The style of the stamen is slender with two lobed stigma. The style is 1/16″ long.

General description: The flowers bloom in one- to six-flower clusters which are axillary, pedicelled and heterostylous. The overall length of the flower is 1″ to 1⅛″.

Stems and Bark:
*Wood current growth.*—Surface texture: Smooth with frequent lenticels. Color of bark: Majolica Yellow #009/2.
*Wood medium growth.*—Surface texture: A few ridges and some veining is apparent and the lenticels are more prominent than current growth. Color of bark: Willow Green Color No. #862/1.
*Wood, mature growth.*—Surface texture: Ridges and veining readily apparent causing surface roughness and lenticels are even more prominent than medium growth. Color of bark: Willow Green Color #862/1. Branches: Hollow with a little pith at the nodes.

I claim:

1. A new and distinct selection of Forsythia as substantially shown and described herein, characterized particularly as to novelty by the unique combination of yellow foliage on the new growth up to 18 inches back on the branches, a dark green mature foliage, two different types of leaf arrangements on the same plant, and yellow blossoms in the spring.

* * * * *